United States Patent
Miki et al.

(10) Patent No.: US 7,223,546 B2
(45) Date of Patent: *May 29, 2007

(54) METHOD FOR MEASURING THE AMOUNT OF CONSTITUENT CONTAINED IN A SPECIFIC LIPOPROTEIN

(75) Inventors: Yutaka Miki, Amagasaki (JP); Toshiro Hanada, Amagasaki (JP); Kiyoko Tanaka, Amagasaki (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 675 days.

This patent is subject to a terminal disclaimer.

(21) Appl. No.: 10/396,477

(22) Filed: Mar. 26, 2003

(65) Prior Publication Data

US 2003/0180809 A1    Sep. 25, 2003

Related U.S. Application Data

(60) Continuation of application No. 09/693,891, filed on Oct. 23, 2003, now abandoned, which is a division of application No. 08/684,298, filed on Jul. 19, 1996, now Pat. No. 6,162,607.

(30) Foreign Application Priority Data

Jul. 21, 1995    (JP) .................................. 07-207663

(51) Int. Cl.
G01N 33/53    (2006.01)

(52) U.S. Cl. ........................... 435/7.1; 435/11; 435/19; 435/25; 435/28; 435/805; 435/962; 436/71; 436/810; 436/824

(58) Field of Classification Search .................... None
See application file for complete search history.

(56) References Cited

U.S. PATENT DOCUMENTS

| | | | |
|---|---|---|---|
| 4,211,530 A | 7/1980 | Goverde et al. | 23/230 B |
| 4,311,788 A | 1/1982 | Heuck | 435/7 |
| 4,746,605 A | 5/1988 | Kerscher et al. | 435/7 |
| 4,892,815 A | 1/1990 | Kerscher et al. | |
| 5,403,745 A | 4/1995 | Ollington et al. | 435/11 |
| 5,407,836 A | 4/1995 | Ziegenhorn et al. | 436/539 |
| 5,490,981 A | 2/1996 | Chiknas | 435/194.1 |
| 5,773,304 A | 6/1998 | Hino et al. | |
| 5,814,472 A | 9/1998 | Miki et al. | |
| 5,925,534 A | 7/1999 | Miki et al. | |

FOREIGN PATENT DOCUMENTS

| | | |
|---|---|---|
| JP | 06242110 A | 9/1994 |
| JP | 7301636 A | 11/1995 |
| JP | 08068795 A | 3/1996 |
| WO | WO 95/24647 | 9/1995 |

*Primary Examiner*—Bao-Thuy L. Nguyen
(74) *Attorney, Agent, or Firm*—Armstrong, Kratz, Quintos Hanson & Brooks, LLP

(57) ABSTRACT

There is provided a method and kit for measuring the amount of an objective constituent contained in a specific lipoprotein in a biological sample such as serum and plasma, specifically for measuring the amount of cholesterol contained in high density lipoprotein, which can be applicable to clinical tests.

4 Claims, No Drawings

METHOD FOR MEASURING THE AMOUNT OF CONSTITUENT CONTAINED IN A SPECIFIC LIPOPROTEIN

This application is a Continuation of prior application Ser. No. 09/693,891, filed Oct. 23, 2000, now abandoned, which is a Divisional of prior application Ser. No. 08/684,298, filed Jul. 19, 1996, now U.S. Pat. No. 6,162,607, which is hereby incorporated by reference.

BACKGROUND OF THE INVENTION

The present invention relates to a method for measuring the amount of an objective constituent for measurement contained in a specific lipoprotein in a biological sample such as serum and plasma. More particularly, the invention provides a method for measuring the amount of cholesterol contained in high density lipoprotein (hereinafter referred to as HDL). The method of the present invention can be applied advantageously to automatically quantitative measurement of HDL cholesterol which has widely been used in the field of clinical tests.

As to methods for measuring the amount of the objective constituent for measurement contained in the specific lipoprotein such as cholesterol contained in HDL, there have been known various methods including ultracentrifugal separation method, electrophoresis method, precipitation method and the like. In the field of clinical tests, the precipitation method has usually and widely been carried out, for the reason that this method can be carried out simply as compared with the ultracentrifugal separation method and the electrophoresis method.

However, a problem with conducting the precipitation method is that this method cannot be carried out only by use of a conventional automatic analyzer, for the reason that this method comprises two steps; (1) a step of pretreatment operation, which comprises, a) mixing a serum with a precipitating agent and forming precipitates of the lipoproteins other than the specific lipoprotein, b) separating the precipitates by centrifugation, and c) collecting thus formed supernatant; and (2) a step of measuring the amount of the objective constituent contained in the specific lipoprotein in the supernatant.

In order to solve the problem, there have been developed some methods; for example Japanese Patent Kokai (Laid-open) No. Hei 6-242110 (1994) discloses a method in that, lipoproteins other than the specific lipoprotein are agglutinated by use of a precipitating agent and/or an antibody reactive to the lipoproteins other than the specific lipoprotein, then the specific constituent in the specific lipoprotein is subjected to reaction with a reagent for quantitative measurement thereof, and thereafter, at the same time, or after the reaction is stopped, the agglutinated lipoprotein is dissolved to give a homogeneous solution, and then the optical absorbance of said solution is measured.

This method, however, requires 3 or 4 kinds of reagents and thus can be applicable only to such remarkably limited automatic analyzers wherein measurement can be conducted with the use of 3 or 4 kinds of reagents, while this method cannot be applied to such automatic analyzers wherein only up to 2 kinds of reagents can be used as conventionally used in clinical tests. Further, this method has the defect of lower reproducibility of measurement because of using 3 or 4 kinds of reagents.

In consideration of the above circumstances, the problem to be solved by the present invention is to provide a method capable of measuring directly the amount of the objective constituents for measurement contained in the specific lipoprotein in a biological sample by using an automatic analyzer, without subjected to any pretreatment operation to separate the specific lipoprotein from other lipoproteins, which has necessarily been carried out in conducting the precipitation method widely used in conventional clinical tests.

SUMMARY OF THE INVENTION

The present invention relates to a method for measuring the amount of an objective constituent for measurement contained in a specific lipoprotein among lipoproteins contained in a biological sample, which comprises mixing a biological sample with an antibody reactive to lipoprotein(s) other than said specific lipoprotein and thereafter measuring the absorbance ($OD_1$) of the reaction mixture, and then mixing said reaction mixture with a reagent for measurement of the objective constituent for measurement contained in the lipoprotein and thereafter measuring again the absorbance ($OD_2$) of the latter reaction mixture and calculating the amount of the objective constituent for the measurement contained in the specific lipoprotein on the basis of the difference between $OD_1$ and $OD_2$.

Furthermore, the present invention relates to a kit for measurement of an objective constituent for measurement contained in the specific lipoprotein, which comprises (i) a reagent composition containing an antibody reactive to lipoprotein(s) other than the specific lipoprotein and a buffering agent and (ii) a reagent composition containing a reagent for measurement of the objective constituent for measurement contained in a lipoprotein and a buffering agent.

DESCRIPTION OF THE PREFERRED EMBODIMENTS

The present inventors have made an extensive research work for finding a method for measuring directly the amount of an objective constituent contained in a specific lipoprotein by use of an automatic analyzer without carrying out any pretreatment operation to remove the lipoproteins other than the specific lipoprotein.

As a result, the inventors have found that measurement of constituent(s) in a specific lipoprotein without previously removing lipoproteins other than the specific lipoprotein is possible by mixing a biological sample with a first reagent solution comprising an antibody reactive to lipoprotein(s) other than the specific lipoprotein to allow a reaction to take place, and thereafter measuring an absorbance ($OD_1$) of the reaction mixture, and then mixing the reaction mixture with a second reagent solution comprising a reagent for measurement of the constituent in the lipoprotein to allow a reaction to take place, and thereafter measuring an absorbance ($OD_2$) of the latter reaction mixture and using thus measured absorbance $OD_1$ and $OD_2$, and on the basis of this discovery, the present invention has been established.

The lipoproteins are classified, according to their specific gravities, into chylomicrons, very low density lipoprotein (VLDL), low density lipoprotein (LDL) and HDL and the like.

In the present invention, any one of these lipoproteins can be selected as the specific lipoprotein to be the object of the measurement. And for measurement of the amount of any specific constituent contained in thus selected specific lipoprotein, first a biological sample is mixed with an antibody reactive to lipoprotein(s) other than the specific lipoprotein to allow a reaction to take place, then the optical absorbance ($OD_1$) of the thus obtained reaction mixture is measured, and next said reaction mixture is mixed with a reagent for measuring the specific constituent for measurement to allow a reaction to take place, then the optical absorbance ($OD_2$) of the latter reaction mixture is measured, and the amount of the objective constituents for measurement contained in the specific lipoprotein is determined based on the measured values of the optical absorbances ($OD_2$) and ($OD_1$), without conducting any operation for removing lipoproteins other than the specific lipoprotein.

In the present invention, the objective constituents for measurement contained in the specific lipoprotein may include but are not limited to cholesterol, triglycerides, phospholipids and the like.

The antibody reactive to lipoprotein(s) other than the specific lipoprotein in the present invention may include any ones such as having an effect of preventing the objective constituents for measurement contained in lipoproteins other than the specific lipoprotein from participating in the reaction with a reagent for measuring the amount of the objective constituents contained in the lipoprotein, and the antibody may be monoclonal antibody or polyclonal antibody, regardless of its origin, so far as it has the effect mentioned above. Taking the degree of the preventing effect into consideration, however, a polyclonal antibody is preferable. When a monoclonal antibody is used, it is preferable to use 2 or 3 kinds or more, preferably 5 kinds or more of monoclonal antibodies which recognize different antigenic determinants from each other. Examples of the preferable antibody in the present invention include an anti-apolipoprotein antibody such as anti-apolipoprotein A, anti-apolipoprotein B, anti-apolipoprotein C and anti-apolipoprotein E, an anti-lipoprotein antibody such as anti-αlipoprotein antibody and anti-βlipoprotein antibody.

The most preferable antibody is selected from those mentioned above, in accordance with the objective lipoprotein(s) for measurement.

For instance, in case of measuring the objective constituents of HDL, the antibody to be used for the purpose of preventing the objective constituent contained in lipoproteins other than HDL from participating in the measuring reaction, may include anti-apolipoprotein B antibody, anti-apolipoprotein C antibody, anti-apolipoprotein E antibody, anti-βlipoprotein antibody and the like.

These antibodies may be used singly or in combination by mixing suitably with any one or more of these, so far as said antibody has the desired preventing effect mentioned above. Furthermore, these antibodies may be those of enzymatically or chemically decomposed or modified types, such as F(ab')2, enzyme-antibody conjugate and hapten-antibody conjugate, and the like.

The antibody of the present invention is one which reacts with lipoprotein(s) other than the specific lipoprotein so as to prevent the objective constituents for measurement contained in lipoproteins other than the specific lipoprotein from participating in the reaction.

Among the antibodies, such ones are preferable that agglutination caused by the reaction of the antibody with lipoprotein(s) other than the specific lipoprotein is not so high as hindering the desired measurement.

The concentration of the antibody reactive to lipoprotein(s) other than the specific lipoprotein, which is to be used, is not specifically restricted, so far as being higher than that capable of preventing the objective constituent for measurement contained in the lipoproteins other than the specific lipoprotein from reacting with the reagent for measuring the objective constituent, and in general, the antibody is added to the first reagent solution so as to keep the concentration thereof in a mixture of the first and the second reagent solutions and the biological sample to be measured in the range of 0.001 to 10 mgAb/ml, preferably 0.01 to 1 mgAb/ml.

It is preferable to incorporate a buffering agent in the reagent solution comprising an antibody.

Any buffering agent can be used, so far as having buffering ability to keep pH 5.0 to 11.0 and not inhibiting the measuring reaction of the objective constituents for measurement, and tris(hydroxymethyl)-aminomethane, Good's buffering agent, phosphates, berates and the like can be exemplified. For instance, the buffering agent to be used for measuring the amount of cholesterol in HDL is exemplified by those having the buffering ability to keep pH 5.7 to 9.1 such as glycine derivatives including N-(2-acetamide)-2-aminoeth-ane sulfonic acid and N-(2-acetamide)-imino-2-acetic acid, hydroxyalkylamine derivatives, more particularly, 2-hydroxyethylamine derivatives including N,N-bis(2-hydroxyethyl)-2-aminoethanesulfonic acid, bis(2-hydroxyethyl) imino-tris(hydroxymethyl)methane,3-[N,N-bis (2-hydroxyethyl)amino]-2-hydroxypropanesulfonic acid and the like, tris(hydroxymethyl)aminomethane, tris(hydroxymethyl)amine derivatives including 3-[N-tris(hydroxymethyl)methylamine]-2-hydroxypropanesul fonic acid, N-tris(hydroxymethyl)-2-aminoethanesulfonic acid and the like, and the hydroxyalkylamine derivatives are, among of them, particularly preferable in view of measuring accuracy. Specifically, in case of using for measuring the amount of cholesterol in HDL, a hydroxyalkylamine derivative is preferable.

The concentration of the buffering agent to be used is generally selected from a range of 10 mM to 1M, preferably 20 to 500 mM.

As the reagent for measuring the amount of the objective constituent, any one of known ones which have been used for measuring the amount of the objective constituent contained in the lipoprotein can be used without any specific limitation. Furthermore, at present, various measuring methods applying enzymes (i.e., for enzymatic methods) have widely been used in this field, and reagents used for such enzymatic methods are advantageously used in the present invention because of their easy availability.

For instance, as the reagent for measuring the amount of cholesterol contained in the lipoprotein, there can be exemplified by those which have been used in known measuring methods, such as reagents for oxidizable-colorimetric method which comprises cholesterol oxidase (COD), cholesterol esterase (CHE), peroxidase (POD), oxidizable color reagents, etc., and reagents for ultraviolet (UV) spectrometric method which comprises CHE, cholesterol dehydrogenase (CHD), nicotinamide adenine dinucleotide (NAD).

As the reagents used for measuring the amount of triglycerides in the lipoprotein, there can be exemplified by those which have been used in known measuring methods such as glycerokinase(GK)-glycerol-3-phosphate oxidase method, glyceroldehydrogenase method and GK-glycerol-3-phosphate dehydrogenase method.

As the reagents used for measuring the amount of phospholipid in the lipoprotein, there can be exemplified by those which have been used in known measuring methods such as an organic solvent extraction method and a method using phospholipase and cholinoxidase.

Each one of these reagents for measuring the amount of the objective constituents is generally comprised in the reagent solution containing no antibody (the 2nd solution), while some of which, for example POD, an oxidizable color reagent and NAD may be comprised in the reagent solution containing the antibody (the 1st solution). The concentration of each one of these reagents to be comprised in the reagent solutions can be suitably selected from such a range as having been used in the measurement in this field.

The reagent solution containing no antibody (the 2nd solution) used in the present invention preferably further comprises a surfactant. The surfactant has the effect of promoting the measurement reaction of the objective constituent contained in the specific lipoprotein, particularly cholesterol, so as to make it possible to shorten the reaction time. The surfactant to be added for this purpose can be, without any limitation, any of nonionic surfactants, amphoteric surfactants, cation surfactants and anion surfactants, so far as they do not hinder the measurement reaction of the objective constituent contained in the specific lipoprotein. The surfactant includes nonionic surfactants such as polyoxyethylene cetyl ether, polyoxyethylene oleyl ether, polyoxyethylene lauryl ether, polyoxyethylene alkylphenyl ether including polyoxyethylene isooctylphenyl ether and polyoxyethylene nonylphenyl ether, and polyethylene glycol monolaurate, and amphoteric surfactants such as stearyl betaine and 2-alkyl-N-carboxymethyl-N-hydroxyethyl imidazolinium betaine, and anion surfactants such as choleic acid, deoxy cholic acid and sodium polyoxyethylene alkylphenol ether sulfate. Among those surfactants, nonionic ones having HLB value of 12 to 17 are preferable in view of the accuracy of the measurement. As the nonionic surfactants used in measurement of cholesterol in HDL, ones having HLB value of 12 to 17 are particularly preferable. Those surfactants can be used alone or in suitable combination.

The concentration of the surfactant to be used is not critical, and in general, it is added to the 2nd solution in such an amount that the final concentration in the mixture of the 1st and the 2nd solutions and the biological sample to be measured is 0.001 to 10 w/v %, preferably 0.01 to 1 w/v %.

It is to be noted that when the surfactant is added to the first solution, measurement error caused by the objective constituent contained in lipoproteins other than the specific lipoprotein may be observed.

An agglutination promoter such as polyethylene glycol and polyvinyl alcohol which has generally been used in measurement method using immunoagglutination reaction, is not required to be present in the 1st or the 2nd solution used in the measurement method of the present invention.

This does not mean, however, that addition of the agglutination promoter should completely be excluded, but the promoter may be incorporated in the 1st and/or the 2nd solution, so far as the amount is such one as not hindering the desired measurement.

The measurement of the present invention is conducted, for instance, as mentioned below.

A biological sample such as serum and/or plasma is mixed with a first solution comprising an antibody reactive to lipoprotein(s) other than the specific lipoprotein and a buffering agent to allow a reaction to take place at 2 to 40° for 3 to 30 minutes, and thereafter an absorbance ($OD_1$) of the reaction mixture is measured. Then, the reaction mixture is mixed with the 2nd solution comprising a reagent for measuring the objective constituent, a buffering agent and if necessary a surfactant, to allow a reaction to take place at 2 to 40° for 3 to 30 minutes, and thereafter an absorbance ($OD_2$) of the latter reaction mixture is measured.

The value of $OD_1$ is subtracted from $OD_2$ to give $OD_3$, and the obtained $OD_3$ is applied to a calibration curve showing the relationship between the concentration of the objective constituent for measurement and $OD_3$, which is previously prepared by conducting the same procedure as above with the use of the same reagents as above on standard solutions containing known amounts of the objective constituent for measurement in the specific lipoprotein, whereby the amount of the objective constituent for measurement in the biological sample is obtained. When the volume of the solution to which measurement of $OD_1$ is conducted is different from that to which the measurement of $OD_2$ is conducted, the $OD_1$ value is corrected in accordance with the difference before being subtracted from $OD_2$.

The kit of the present invention for measuring the amount of an objective constituent in a specific lipoprotein comprises (i) a reagent composition (the first reagent composition) comprising an antibody reactive to lipoprotein(s) other than the specific lipoprotein and a buffering agent, and (ii) a reagent composition (the second reagent composition) comprising the reagent for measuring the amount of objective constituent in the specific lipoprotein, a buffering agent and if necessary a surfactant, and the preferable embodiments of those components are as mentioned before.

A part of the components usually contained in the second reagent composition may be incorporated in the first reagent composition, so far as no hindering effect to the measurement is observed. For instance, when cholesterol in the specific lipoprotein is measured by an enzymatic method with the use of cholesterol oxidase (COD), cholesterol esterase (CHE), peroxidase (POD), a reagent developing color by coupling with 4-aminoantipyrine by the act of 4-aminoantipyrine and an oxidizing agent (hereinafter abbreviated as coloring reagent) as the reagent for measurement of cholesterol, it is essential to incorporate an antibody against lipoprotein(s) other than the specific lipoprotein and a buffering agent in the first reagent composition and to incorporate COD and CHE in the second reagent composition, and the second reagent composition preferably contains also a surfactant, but other components may be incorporated in the first or second reagent composition.

From view point of stability of the reagent compositions, use is preferably made of a combination of the first reagent composition incorporated with an antibody against lipoprotein(s) other than the specific lipoprotein, a buffering agent and 4-aminoantipyrine and the second reagent composition incorporated with COD, CHE, POD, a coloring reagent, a buffering agent and a surfactant.

In the following, the present invention is further explained in details with citation of Examples and Reference examples, but the present invention is not limited to those examples in any way.

Abbreviations used in the examples mean as follow.
BES: N,N-bis(2-hydroxyethyl)-2-aminoethansulfonic acid
COD: cholesterol oxidase CHE: cholesterol esterase
POD: peroxidase
DAOS: N-ethyl-N-(2-hydroxy-3-sulfopropyl)-3,5-dimethoxyanaline
Triton X-100 (Trade Name; manufactured and sold by Rohm & Haas): polyoxyethylene alkylphenyl ether (HLB: 13.5)
ACES: N-(2-acetamido)-2-aminoethanesulfonic acid
Emalex NPL-30 (Trade Name; manufactured and sold by Nihon Emulsion Co.): polyoxyethylene nonylphenyl ether (HLB: 17)
Triton X-405 (Trade Name; manufactured and sold by Rohm & Haas): polyoxyethylene alkylphenyl ether (HLB: 17.9)

EXAMPLE 1

Amount of cholesterol comprised in HDL in serum was measured by the method of the present invention with the use of an automatic analyzer Hitachi 7150 (Trade Name; manufactured and sold by Hitachi Ltd.).

[Samples]

10 samples of fresh human serum.

[Reagents]

| 1st reagent (R-1): | |
| --- | --- |
| Antiserum to βlipoprotein (12 mgAb/ml, manufactured and sold by Wako Pure Chemical Industries, Ltd.) | 1% w/v |
| 4-Aminoantipyrine | 1 mM |
| BES-NaOH buffer solution (pH 7.0) | 100 mM |
| 2nd Reagent (R-2): | |
| COD | 3 Units /ml |
| CHE | 3 Units /ml |
| POD | 1 Unit / ml |
| DAOS | 1 mM |
| Triton X-100 | 0.05% w/v |
| BES-NaOH buffer solution (pH 7.0) | 100 mM |

[Measuring Parameters (Measuring Conditions)]

| Measurement method: 2 Point end method [24]–[50] | |
| --- | --- |
| Sample volume: | 4 μl |
| R-1 volume: | 270 μl |
| R-2 volume: | 90 μl |
| Measurement wave length: | 700/600 nm |
| Measurement temperature: | 37° C. |

[Results]

The measurement result is shown in the table 1.

EXAMPLE 2

Amount of cholesterol contained in HDL in serum was measured by the method of the present invention with the use of an automatic analyzer Hitachi 7150 (Trade Name; manufactured and sold by Hitachi Ltd.).

[Samples]

Same as Example 1.

[Reagents]

| 1st reagent (R-1): | |
| --- | --- |
| Antiserum to βlipoprotein (12 mgAb/ml, manufactured and sold by Wako Pure Chemical Industries Ltd.) | 1% w/v |
| 4-Aminoantipyrine | 1 mM |
| ACES-NaOH buffer solution (pH 7.0) | 100 mM |
| 2nd reagent (R-2): | |
| COD | 3 Unit /ml |
| CHE | 3 Unit /ml |
| POD | 1 Unit /ml |
| DAOS | 1 mM |
| Triton X-100 | 0.05% w/v |
| ACES-NaOH buffer solution (pH 7.0) | 100 mM |

[Measuring Parameters (Measuring Conditions)]

Same as Example 1.

[Results]

The measurement results is also shown in the table 1.

Reference Example 1

On the serum samples used in Example 1, cholesterol contained in HDL was measured by known phosphorus-tungstic acid/magnesium salt precipitation method with the use of HDL-Cholesterol E-Test Wako (Trade Name; manufactured and sold by Wako Pure Chemical Industries Ltd.).

The measurement procedure was as the standard procedure explained in the brochure of said kit.

[Results ]

The measurement result is also shown in the table 1.

TABLE 1

| Sample No. | Example 1 (mg/dl) | Example 2 (mg/dl) | Reference Example 1 (mg/dl) |
| --- | --- | --- | --- |
| 1 | 56.3 | 60.7 | 55.1 |
| 2 | 38.5 | 46.2 | 37.3 |
| 3 | 53.3 | 59.4 | 54.7 |
| 4 | 47.5 | 45.0 | 45.8 |
| 5 | 48.8 | 54.6 | 47.2 |
| 6 | 44.7 | 47.6 | 42.1 |
| 7 | 62.4 | 70.5 | 63.7 |
| 8 | 74.2 | 79.5 | 66.9 |
| 9 | 44.9 | 53.7 | 41.0 |
| 10 | 53.1 | 56.6 | 52.2 |
| Average Value | 52.4 | 57.4 | 50.6 |
| Coefficient of correlation to Reference Example 1 | 0.969 | 0.931 | — |

From the result in the Table 1, it can be shown that the measurement value of cholesterol in HDL by the method of the present invention shows high correlation with that obtained by the method of Reference Example 1 (conventional method).

The measurement values obtained by the method of the present invention are higher than those obtained In Reference Example 1. On the other hand, it has been known that the value of cholesterol in HDL by the method in Reference Example 1, phosphotungstic acid/magnesium salt precipitation method, is rather lower than that obtained by the standard method, ultracentrifugal separation method. Therefore, the measured values of cholesterol obtained by method of the present invention (particularly, by Example 1) are considered close to the measured values obtained by the standard method.

EXAMPLE 3

Amount of cholesterol contained in HDL in serum was measured by the method of the present invention with the use of an automatic analyzer Hitachi 7150 (Trade Name; manufactured and sold by Hitachi Ltd.).

[Samples]

10 Samples of fresh human serum.

[Reagents]

| 1st reagent (R-1): | |
|---|---|
| Antiserum to apolipoprotein B (12 mgAb/ml, manufactured and sold by Boehringer Mannheim GmbH.) | 3% w/v |
| 4-Aminoantipyrine | 1 mM |
| Tris-HCl buffer solution (pH 7.2) | 100 mM |
| 2nd reagent (R-2): | |
| COD | 3 Unit /ml |
| CHE | 3 Unit /ml |
| POD | 1 Unit /ml |
| DAOS | 1 mM |
| Emalex NPL-30 | 0.05% w/v |
| Tris-HCl buffer solution (pH 7.2) | 100 mM |

[Measuring Parameters (Measuring Conditions)]

Measurement method: 2 Point-end method [16]-[34]

| | |
|---|---|
| Sample volume: | 4 μl |
| R-1 volume: | 270 μl |
| R-2 volume: | 90 μl |
| Measurement wave length: | 700/600 nm |
| Measurement temperature: | 37° C. |

[Results]

The measurement result is shown in the table 2.

EXAMPLE 4

Amount of cholesterol contained in HDL in serum was measured by the method of the present invention with the use of an automatic analyzer Hitachi 7150 (Trade Name; manufactured and sold by Hitachi Ltd.).

[Samples]

Same as Example 3.

[Reagents]

| 1st reagent (R-1): | |
|---|---|
| Antiserum to apolipoprotein B (12 mgAb/ml, manufactured and sold by Boehringer Mannheim GmbH.) | 3% w/v |
| 4-Aminoantipyrine | 1 mM |
| Tris-HCl buffer solution (pH 7.2) | 100 mM |
| 2nd reagent (R-2): | |
| COD | 3 Unit /ml |
| CHE | 3 Unit /ml |
| POD | 1 Unit /ml |
| DAOS | 1 mM |
| Triton X-405 | 0.1% w/v |
| Tris-HCl buffer solution (pH 7.2) | 100 mM |

[Measuring Parameters (Measuring Conditions)]

Same as Example 3.

[Results]

The measurement result is also shown in the table 2.

Reference Example 2

On the serum samples used in Example 3, cholesterol contained in HDL was measured by known phosphorus-tungstic acid/magnesium salt precipitation method with the use of HDL-Cholesterol E-Test Wako (Trade Name; manufactured and sold by Wako Pure Chemical Industries, Ltd.).

The measurement procedure was as the standard procedure explained in the brochure of said kit.

[Results]

The measurement results is also shown in the table 2.

TABLE 2

| Sample No. | Example 3 (mg/dl) | Example 4 (mg/dl) | Reference Example 2 (mg/dl) |
|---|---|---|---|
| 11 | 48.4 | 38.6 | 47.2 |
| 12 | 44.7 | 37.6 | 42.1 |
| 13 | 66.5 | 54.1 | 66.9 |
| 14 | 56.6 | 45.5 | 52.6 |
| 15 | 43.5 | 40.2 | 41.8 |
| 16 | 36.1 | 37.6 | 34.2 |
| 17 | 56.3 | 45.1 | 54.2 |
| 18 | 37.8 | 34.2 | 36.9 |
| 19 | 51.3 | 44.6 | 47.2 |
| 20 | 33.0 | 30.4 | 33.6 |
| Average Value | 47.4 | 40.8 | 45.7 |
| Coefficient of correlation to Reference Example 2 | 0.989 | 0.939 | — |

From the result in the Table 2, it can be shown that the measurement value of cholesterol in HDL by the method of the present invention shows high correlation with that obtained by the method of Reference Example 2 (conventional method).

As can be clearly understood from the disclosure in the specification, the present invention provides a method for measuring the objective constituents contained in the specific lipoprotein, in a biological sample, capable to apply directly to an automatic analyzer without carrying out any pretreatment operation for removing lipoproteins other than the specific lipoprotein. By applying the present invention, (i) the amount of one or more objective constituents contained in a specific lipoprotein can be measured by use of a conventional type of automatic analyzer because the measurement can be carried out by using only 2 kinds of reagent solutions, moreover, high accuracy measurement is conducted because the measured values are obtained with excellent reproducibility; (ii) the measurement in the present invention is conducted by 2-point end method, because, it is not required to conduct the step of re-dissolving the agglutinated lipoproteins other than the specific lipoprotein to measure the optical absorbance of a uniform solution for measuring the objective constituent contained in the specific lipoprotein. Also, the present invention provides advantageous effect to avoid any adverse effect to the measurement of optical absorbance caused by co-existed substances contained in the biological sample, thus the present invention contributes greatly in this field.

What is claimed:

1. A kit for measurement, by two point-end assay by using an autoanalyzer, of cholesterol contained in the class of high density lipoproteins in a biological sample containing at least one other class of lipoprotein selected from the group consisting of the chylomicrons class, the class of very low density lipoproteins and the class of low density lipoproteins, said kit for measurement comprising:
- a first reagent composition comprising (i) a buffering agent, (ii) an antibody which does not bind with the class of high density lipoproteins but which binds with said at least one other class of lipoprotein contained in the biological sample to start an antibody bonding reaction and (iii) peroxidase, said antibody substantially preventing the cholesterol in said at least one other class of lipoproteins from participating in a reaction for measurement of cholesterol, wherein said first reagent composition does not contain cholesterol esterase and/or cholesterol oxidase;
- a second reagent composition separate from said first reagent composition, containing no antibody and comprising (i) a buffering agent, (ii) cholesterol oxidase and (iii) cholesterol esterase; and
- 4-aminoantipyrine and a reagent developing color by coupling with 4-aminoantipyrine, wherein one of these is incorporated in the first reagent composition and the other is incorporated in the second reagent composition.

2. A kit for measurement, by two point-end assay by using an autoanalyzer, of cholesterol contained in the class of high density lipoproteins in a biological sample containing at least one other class of lipoprotein is selected from the group consisting of the chylomicrons class, the class of very low density lipoproteins and the class of low density lipoproteins, said kit for measurement comprises:
- a first reagent composition comprising (i) a buffering agent, (ii) an antibody which does not bind with the class of high density lipoproteins but which binds with said at least one other class of lipoprotein contained in the biological sample to start an antibody binding reaction, (iii) 4-aminoantipyrine and (iv) peroxidase, said antibody substantially preventing the cholesterol in said at least one other class of lipoproteins from participating in a reaction for measurement of cholesterol, wherein said first reagent composition does not contain cholesterol esterase and/or cholesterol oxidase;
- a second reagent composition separate from said first reagent composition, containing no antibody and comprising (i) a buffering agent, (ii) cholesterol oxidase, (iii) cholesterol esterase and (iv) a reagent developing color by coupling with 4-aminoantipyrine.

3. The kit as claimed in claim 1 or 2, wherein the antibody is at least one selected from the group consisting of anti-apolipoprotein A, anti-apolipoprotein B, anti-apolipoprotein C, anti-apolipoprotein E, anti-αlipoprotein antibody and anti-βlipoprotein antibody.

4. The kit as claimed in claim 1 or 2, wherein the concentration of the antibody is 0.001 to 10 mgAb/ml.

* * * * *